Figure 1:
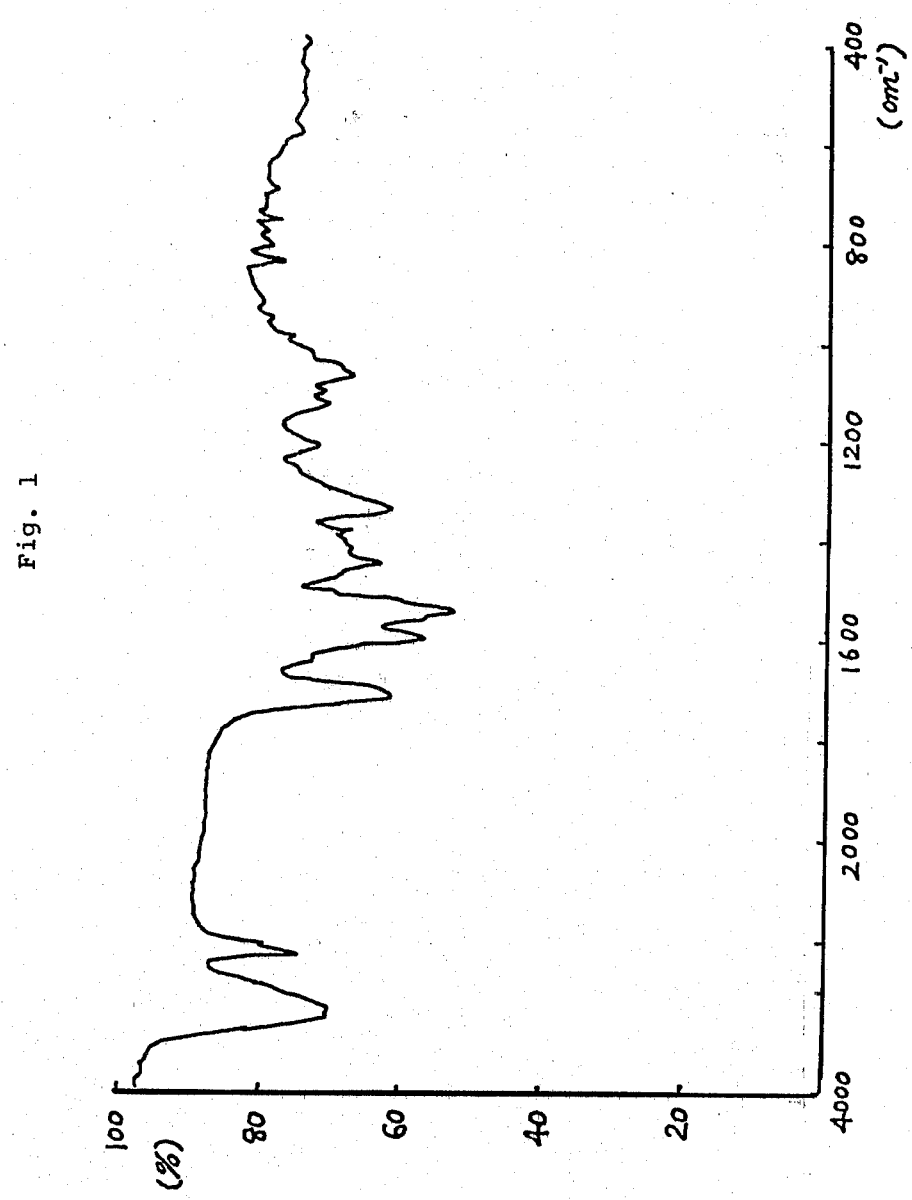

United States Patent [19]

Kasai et al.

[11] 4,395,558
[45] Jul. 26, 1983

[54] 9-EPI-MITOMYCIN B AND D COMPOUNDS

[75] Inventors: Masaji Kasai, Rockville, Md.; Kunikatsu Shirahata; Motomichi Kono, both of Machida, Japan

[73] Assignee: Kyowa Hakko Kogyo Kabushiki Kaisha, Tokyo, Japan

[21] Appl. No.: 323,847

[22] Filed: Nov. 23, 1981

Related U.S. Application Data

[63] Continuation-in-part of Ser. No. 180,553, Aug. 22, 1980, abandoned.

[30] Foreign Application Priority Data

Aug. 24, 1979 [JP] Japan .................................. 54-107069

[51] Int. Cl.³ .................... A61K 31/40; C07D 487/04
[52] U.S. Cl. .................................. 548/422; 424/274
[58] Field of Search .................... 260/326.24; 548/422

[56] References Cited

U.S. PATENT DOCUMENTS 3,738,998 6/1973 Uzu et al. ...................... 260/326.24
4,264,504 4/1981 Urakawa et al. ................ 548/422

FOREIGN PATENT DOCUMENTS 56-30978 3/1981 Japan .................................. 548/422

Primary Examiner—Alton D. Rollins
Attorney, Agent, or Firm—Wolder, Gross & Yavner

[57] ABSTRACT

Mitomycin compounds of the general formula (I):

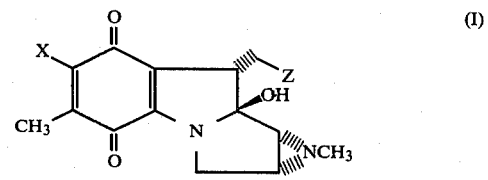

wherein X is selected from an alkoxy group having 1 to 4 carbon atoms and amino group; and Z is selected from —OH, —OCONH$_2$ and —OCO$_2$C$_6$H$_5$ groups. The compounds of this formula may be used as starting materials for the preparation of various mitomycin compounds. When X is as hereinbefore defined and Z is —OCONH$_2$, the compounds exhibit antibacterial activity and are of potential interest as medicaments. Preferred examples of the compounds are 9-Epi-mitomycin B and 9-epi-mitomycin D. The compounds of the formula (I) may be obtained from known mitomycin B or mitomycin D.

4 Claims, 2 Drawing Figures

9-EPI-MITOMYCIN B AND D COMPOUNDS

RELATED ALLICATION

This application is a continuation-in-part of U.S. Ser. No. 180,553 filed Aug. 22, 1980, now abandoned.

BACKGROUND OF THE INVENTION

This invention relates to new mitomycin compounds and processes for producing the same. Mitomycin compounds are known compounds having antibacterial and anti-tumour activities. Typical mitomycin compounds are represented by the following formula:

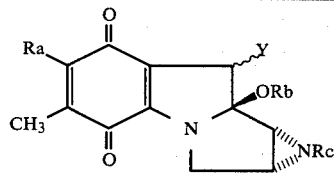

|      |                      | Ra              | Rb              | Rc              | Y     |
|------|----------------------|-----------------|-----------------|-----------------|-------|
| (1)  | Mitomycin A          | OCH$_3$         | CH$_3$          | H               | Y$_1$ |
| (2)  | B                    | OCH$_3$         | H               | CH$_3$          | Y$_2$ |
| (3)  | C                    | NH$_2$          | CH$_3$          | H               | Y$_1$ |
| (4)  | D                    | NH$_2$          | H               | CH$_3$          | Y$_2$ |
| (5)  | E                    | NH$_2$          | CH$_3$          | CH$_3$          | Y$_2$ |
| (6)  | F                    | OCH$_3$         | CH$_3$          | CH$_3$          | Y$_1$ |
| (7)  | G                    | NH$_2$          | CH$_3$          | CH$_3$          | Y$_3$ |
| (8)  | H                    | OCH$_3$         | H               | CH$_3$          | Y$_3$ |
| (9)  | J                    | OCH$_3$         | CH$_3$          | CH$_3$          | Y$_2$ |
| (10) | K                    | OCH$_3$         | CH$_3$          | CH$_3$          | Y$_3$ |
| (11) | Porfiromycin         | NH$_2$          | CH$_3$          | CH$_3$          | Y$_1$ |
| (12) | 1a-N—demethyl-mytomycin K | OCH$_3$    | CH$_3$          | H               | Y$_3$ |
| (13) | 1a-N—demethyl-mitomycin G | NH$_2$     | CH$_3$          | H               | Y$_3$ |

[Notes:-]

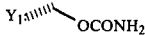
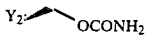

Compounds 1-11 are disclosed in Japanese prior art literatures as follows:

| Compounds 1-11 are disclosed in Japanese prior art literatures as follows: | |
|---|---|
| 1, 2, 3 & 11 | Patent Publications 7597/59, 17897/50 and 23097/63;* |
| 4 & 5 | Patent Application published as 122797/79;* |
| 6 & 9 | Patent Application published as 45322/80;* |
| 7, 8 & 10 | Patent Application published as 15408/80.* |
| 12 & 13 | Patent Application published as 7789/81.* |

[*Laid open to public inspection]

SUMMARY OF THE INVENTION

The present invention is concerned with a new class of mitomycin compounds and the process for producing the same. Various of such new compounds exhibit high antibacterial activity.

It is therefore an object of this invention to provide new mitomycin compounds and processes for producing the same.

According to this invention, we provide new mitomycin compounds represented by the following formula (I):

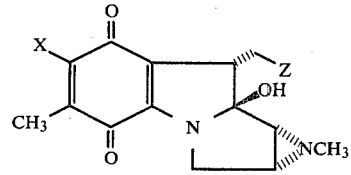

wherein X is selected from an alkoxy group, amino group and alkylamino group and Z is selected from a hydroxy group, —OCONH$_2$ and —OCO$_2$C$_6$H$_5$. In the compounds of the formula (I), X may be a lower alkoxy group having 1 to 4 carbon atoms such as methoxy, ethoxy, n-propoxy, i-propoxy, n-butoxy, t-butoxy and the like, and the alkyl in the alkylamino group may be one having 1 to 4 carbon atoms such as methyl, ethyl, n-propoxy, i-propyl, n-butyl, t-butyl and the like; and the alkylamino group may includes mono- or dialkyl amino group.

The compounds of formula (I) may be used as a starting material for the preparation of various mitomycin compounds of the known types. Moreover, it has also been found that the compounds of the following formula (V) i.e. the compounds of formula (I) wherein X is as hereinbefore defined and Z is —OCONH$_2$ exhibit per se high antibacterial activity.

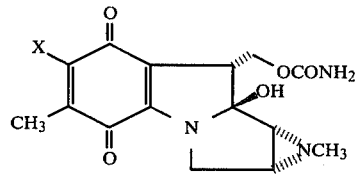

9-Epi-mitomycin B and 9-epi-mitomycin D are preferred examples of the compounds of formula (V) wherein in X is CH$_3$O and NH$_2$, respectively. Thus, the compounds of formula (V), especially 9-epi-mitomycin B and 9-epi-mitomycin D are of potential interest as medicaments.

The following table indicates that 9-epi-mitomycin B and 9-epi-mitomycin D exhibit high inhibiting activity against the growth of various microorganisms.

TABLE 1

Minimum growth inhibitory concentration (μg/ml) by agar dilution method at pH 7.0
Va-1: 9-Epi-mitomycin D
Vb-1: 9-Epi-mitomycin B
M-B: Mitomycin B
M-C: Mitomycin C
M-D: Mitomycin D

| Microorganism | Va-1 | Vb-1 | M-B | M-C | M-D |
|---|---|---|---|---|---|
| Serratia marcescens ATCC 4003 | >50 | 3.1 | 2.5 | 5.0 | — |
| Pseudomonas cepacia ATCC 25608 | >50 | 25 | 10 | 10 | — |
| Staphylococcus aureus ATCC 6538P | 25 | 0.049 | 0.039 | 0.156 | 50 |
| Escherichia coli ATCC 26 | — | 12.5 | >10 | 10 | >50 |
| Bacillus subtilis #10707 | 6.3 | <0.024 | 0.020 | 0.020 | 6.3 |
| Proteus vulgaris ATCC 6897 | 12.5 | 0.049 | 0.078 | 0.078 | 25 |
| Shigella sonnei ATCC 9290 | >50 | 6.3 | 5.0 | 5.0 | 50 |

TABLE 1-continued

Minimum growth inhibitory concentration (μg/ml)
by agar dilution method at pH 7.0
Va-1: 9-Epi-mitomycin D
Vb-1: 9-Epi-mitomycin B
M-B: Mitomycin B
M-C: Mitomycin C
M-D: Mitomycin D

| Microorganism | Va-1 | Vb-1 | M-B | M-C | M-D |
|---|---|---|---|---|---|
| Salmonella typhosa ATCC 9992 | >50 | 6.3 | 10.0 | 5.0 | >50 |
| Klebsiella pneumoniae ATCC 10031 | 3.1 | <0.024 | 0.16 | 0.0098 | 6.3 |

The following table shows the $LD_{50}$ values of 9-epi-mitomycin B, 9-epi-mitomycin D and some known mitomycin compounds.

TABLE 2

| $LD_{50}$ (mouse, ip.) (mg/kg) | |
|---|---|
| 9-epi-mitomycin B | 7.5 |
| 9-epi-mitomycin D | 150 |
| mitomycin B | 4.5 |
| mitomycin D | 430 |

The compounds of formula (I) are new compounds which may be synthesized from the known compound through the intermediates which are also new compounds. In the following specification, the preparation of the compounds of the formula will clearly be described, from which it is understood that the compounds of formula (I) may readily be be prepared by using other methods.

The following diagram indicates that the compounds of formula (V) may be prepared from a known mitomycin compound through the intermediates i.e. the compounds of formulas (IIIe) and (IV) are also new compounds. In addition to such a conversion route, the mutual conversion between the amino or alkylamino group and the alkoxy group of the compounds of formula (V) is also indicated in this diagram, wherein X is as hereinbefore defined, Xa is selected from an amino group and alkylamino group, Xb is an alkoxy group, and R is an alkyl group. The compound of formula Vc is a new compound which is believed to present in the reaction mixture as hereinafter described. The compound of formula II is a known compound selected from mitomycin D (when X is $NH_2$) and mitomycin B (when X is $CH_3O$).

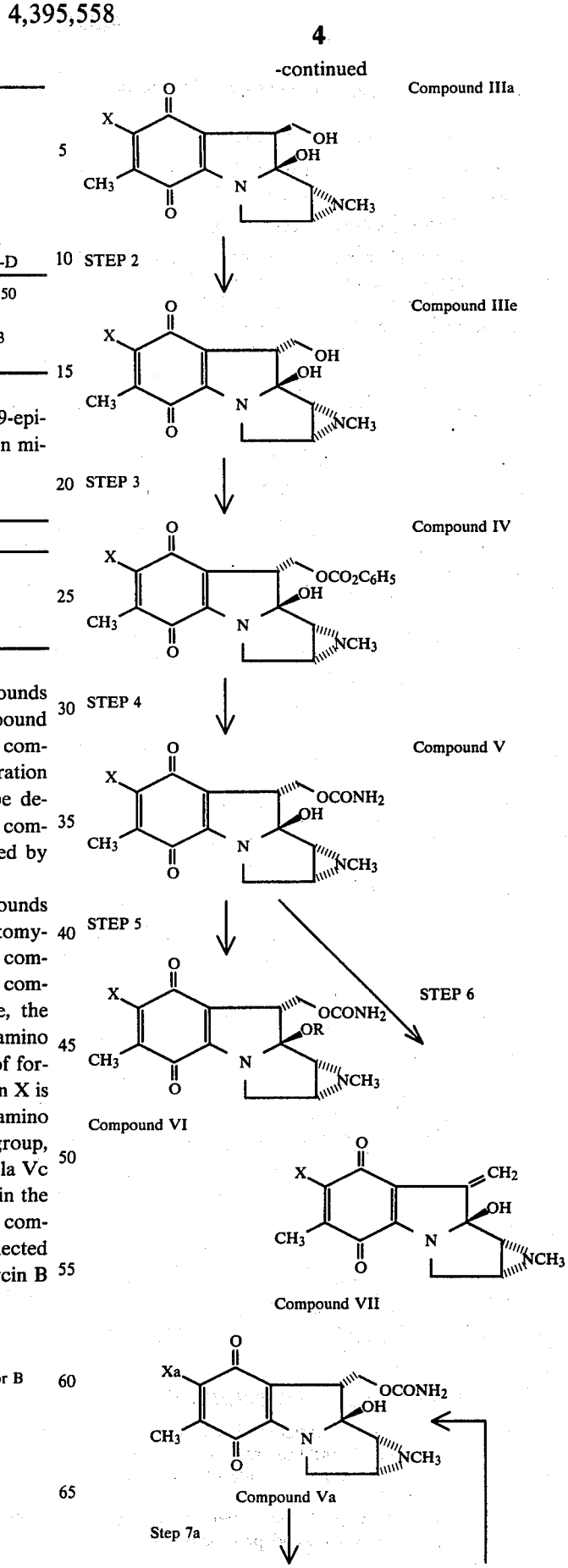

-continued

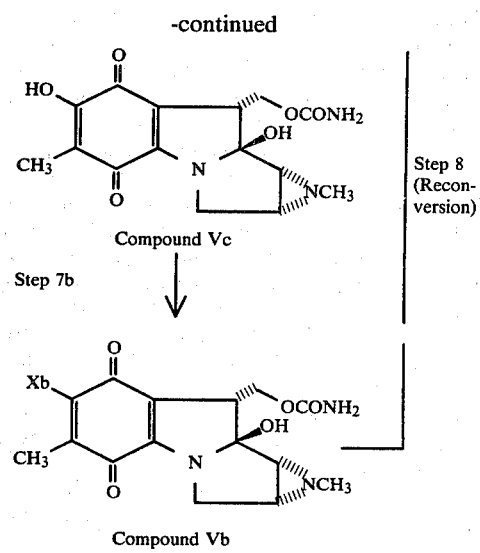

Compound Vc

Step 7b

Compound Vb

Step 8
(Reconversion)

[Step 1]

Compound IIIa may be obtained from the known Compound II i.e. mitomycin B or mitomycin D in a conventional manner such as e.g. the lithium-aluminum hydride method (Japanese patent publication No. 31229/71), alkaline hydrolysis method (Japanese patent publication No. 23558/72), sodium alcoholate method (Japanese patent publication No. 24650/72) and the like. The sodium alcoholate method will be exemplified in the following.

Compound II is treated by using an alcoholate of a primary, secondary or tertiary alcohol in an organic solvent such as e.g. alcohol, tetrahydrofuran, dioxane, dimethylformamide, benzene and the like which may be used alone or in combination. The amounts of the alcoholate and solvent may be about 1–100 mol and 100–1000 mol per one mol of the starting compound, respectively. The reaction is usually effected for several hours to several days, depending upon the types of the solvent and alcoholate used. After completion of the reaction, dry ice is excessively added to the reaction mixture for neutralization. The mixture is then filtered and the filtrate is concentrated in vacuo, followed by purification by suitable methods used in the art of organic synthesis such as e.g. column chromatography, thin layer chromatography for separation, recrystallization and the like. The use of mitomycin B as starting material for this step is described in Example 5 of Japanese patent publication No. 24560/72.

[Step 2]

Compound IIIe is obtained when Compound IIIa is treated with a base in an inert organic solvent to epimerize the hydroxymethyl group at the 9th position. The solvents which may be used alone or in combination for the reaction are exemplified by alcohol, tetrahydrofuran, 1,2-dimethoxyethane, dioxane, dimethylformamide, benzene and the like. The bases which may be used include inorganic bases such as e.g. sodium hydroxide, potassium hydroxide, sodium hydride and the like and organic bases such as e.g. sodium methoxide, sodium ethoxide, potassium t-butoxide, 1,5-diazabicyclo[5,4,-0]undec-5-ene and the like. Per one mol of Compound IIIa, 1–100 mol of the base and 100–1000 mol of the solvent may be used. The reaction proceeds at a temperature of from ambient to 80° C. and is completed in several hours to several days, depending upon the types of the base used. The treatment after completion of the reaction may vary with the base used. Usually, water is added to the reaction mixture and the desired compound is extracted by using an organic solvent, which may be purified by the method as hereinbefore described in Step 1.

[Step 3]

Compound IV may be obtained when Compound IIIe is reacted with a theoretical or excessive amount of a phenoxycarbonyl halide derivative such as phenyl chloroformate. The type and amount of the solvent used are similar to those described in Step 2.

The bases which may be used for the reaction are exemplified by triethylamine, pyridine and the like which may also be used as the solvent. The amount of the amine is usually 1–200 mol based on one mol of the starting compound. The reaction is effected at −10° to 50° C., preferably by cooling with ice, and continued for several hours. After completion of the reaction, water is added to the reaction mixture and the desired compound is extracted by using a similar organic solvent, followed by purification which may be effected in a similar manner to Step 1. An analogous step to this step is disclosed in Japanese patent publication No. 17279/74.

[Step 4]

Compound V may be obtained by carbamoylation of Compound IV. For this purpose, Compound IV is dissolved in an organic solvent, the type and amount of which are analogous to those described in Step 2. The reaction is effected at a temperature of from −70° C. to ambient addition of ammonia. The reaction is completed in several hours, and then unreacted ammonia is removed from the reaction mixture by evaporation in vacuo. The residue is, if desired, purified, for example, by silica gel column chromatography. The crystals of the desired compound may be obtained by recrystallization from a suitable solvent.

Similar reactions to those of Steps 3 and 4 are described, for example, in Journal of Medicinal Chemistry, Vol. 14, No. 2, p.103 (1971), Journal of Am. Chem. Soc., Vol. 99, No. 14, 4835 and Vol. 99, No. 24, 8115 (1977) etc.

[Step 5]

Compound VI may be obtained when Compound V is dissolved in an inert organic solvent and subjected to alkylation by using a suitable alkylating agent such as e.g. an alkyl halide, dialkyl sulfate and the like in the presence of a base. The type and amount of the solvents which may be used alone or in combination are analogous to those described in Step 2. Based upon one mol of the starting compound V, 1–100 mol of the base and 1–100 mol of the alkylating agent may be used. The reaction proceeds at a temperature from −50° C. to ambient for several hours. After completion of the reaction, the reaction mixture is purified in a similar manner to that described in Step 2. An analogous step is disclosed, for example, in Japanese patent publication No. 42269/72.

The conversion of the X in Compound VI may be possible in a similar manner to that described in Steps 7 and 8. Also the conversion of porfiromycin i.e. Compound VI (wherein X is an amino group and R is a methyl group) into mitomycin F (X=methoxy and R=methyl) is carried out in a similar manner to that described, for example, in J. of Medicinal Chem., Vol. 20, No. 6. p.767 (1977).

[Step 6]

Compound VII may be obtained by eliminating carbamic acid from Compound V in an inert solvent in the presence of a base. The solvents which may be used alone or in combination are analogous to those described in Step 2. The bases which may be used are exemplified by sodium carbonate, sodium hydroxide, potassium hydroxide, sodium hydride and other inorganic bases as well as sodium methoxide, potassium t-butoxide, 1,5-diazabicyclo[5,4,0]undec-5-ene and other organic bases, although it is preferred to use a strong base such as e.g. sodium methoxide, potassium t-butoxide, 1,5-diazabicyclo[5,4,0]undec-5-ene and the like. Based upon one mol of the starting compound, 100–1000 mol of the solvent, 1–100 mol of the base may be used. The reaction proceeds at a temperature of from −30° C. to ambient and completes in several hours to several days, depending upon the types of the materials used and reaction temperature. After completion of the reaction, the reaction mixture may be purified by the method as hereinbefore described in Step 1. This step is analogous to the method described in Japanese Patent Application laid open to public inspection as No. 15048/80.

[Steps 7a and 7b]

Compound Vc may be obtained when Compound Va is hydrolysed in a basic aqueous solution so as to introduce a hydroxy group into its 7th position. Compound Vb may be obtained when the above-mentioned reaction mixture is subjected to the reaction with an alkylating agent such as e.g. diazoalkane, alkyl halide, dialkyl sulfate and the like in an organic solvent e.g. ethyl ether, ethyl acetate, methanol and the like. About 100–1000 mol of the solvent and about 1–100 mol of the base may be used per one mol of the starting compound.

Such an organic or inorganic base may be used as an acid-acceptor when acid is by-produced during the reaction. After completion of the reaction, the reaction mixture may be purified, for example, by a similar method to that hereinbefore described in Step 1. An analogous reaction to the reaction in this step is disclosed, for example, in Japanese Patent Publication No. 22380/67.

[Step 8]

Compound Va may be obtained when Compound Vb is dissolved in an organic solvent such as e.g. methanol, ethanol, dimethylformamide and the like or in water, and ammonia or a primary or secondary amine is added to the mixture to carry out the reaction. These solvents may be used alone or in combination at a convenient mixing ratio. The reaction is effected at a temperature from 0° C. to the boiling point of the solvent to results in a compound corresponding to the use amine. Per one mol of the starting compound, the amount of the solvent may be 100–1000 mol and the amount of the amine may be more than the theoretical amount, although it is possible to use an excessive amount of the amine if desired. An analogous reaction to this step is disclosed, for example, in Japanese Patent Publication 43560/72.

Figure 2:
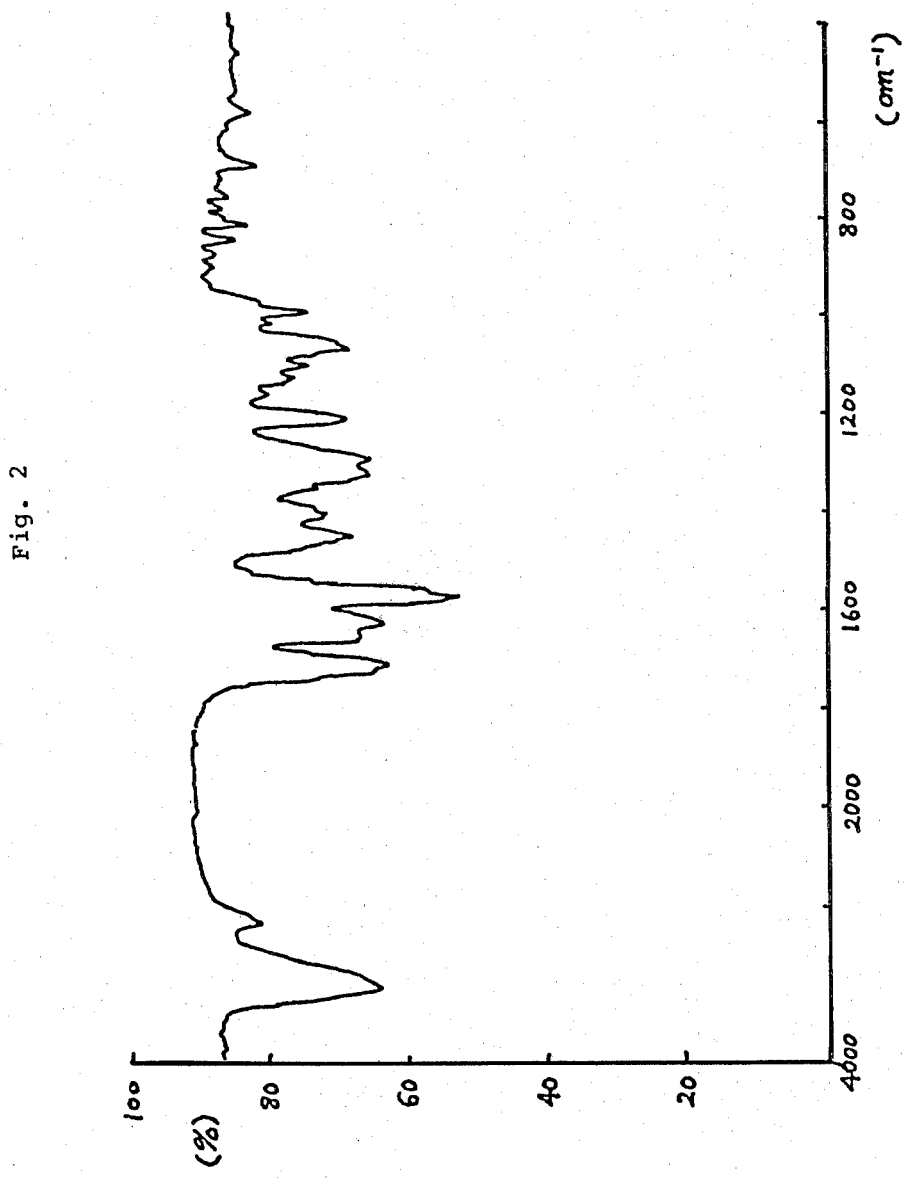

Drawings:

FIGS. 1 and 2 show respectively the infrared absorption spectra of 9-epi-mitomycin D and 9-epi-mitomycin B.

The following non-limiting examples illustrate the invention.

EXAMPLE 1

10-Decarbamoyl-mitomycin D [Step 1]:

Sodium (2.44 g) was dissolved in isopropanol (225 ml). To the solution was added mitomycin D (7-amino-7-demethoxy mitomycin B; 1.93 g) and the mixture was stirred for 22 hours at ambient temperature. The reaction mixture was neutralized with an excessive amount of dry ice and the resultant precipitate was separated by filtration. The filtrate was concentrated under reduced pressure to give a residue which was purified by subjecting to silica gel chromatography using a mixed solvent of chloroform and methanol (95:5 to 9:1 v/v). The fractions containing the desired compounds were collected and combined. The combined fractions were concentrated, and the concentrate was transferred to a column packed with almumina and treated with a mixture of chloroform and methanol (96:4 v/v) as eluting solution. The eluate was concentrated to dryness. By recrystallizing from methanol and ethyl acetate, blackish purple prism crystals were obtained (125 mg; yield 8.1%) having the following physical characteristics.

Mass spectrum: molecular ion peak at m/e 291.

PMR spectrum (in Py.-$d_5$; δppm):

1.90 (s, 3H), 2.19 (s, 3H), 2.21 (dd, 1H), 2.49 (d, 1H), 3.60 (dd, 1H), 3.98 (t, 1H), 4.41 (d, 1H), 4.51 (dd, 1H), 4.69 (dd, 1H)

IR spectrum (KBr tablet method, $cm^{-1}$):

3320 (s), 1586 (s), 1536 (vs), 1440 (s), 1348 (s).

From these characteristics, this substance was identified as 10-decarbamoylmitomycin D.

9-epi-10-decarbamoylmitomycin D [Step 2]:

10-decarbamoylmitomycin D (8 mg) was dissolved in tetrahydrofuran (2 ml). After addition of 1,5-diazabicyclo[5,4,0]undec-5-ene (190 mg), the solution was refluxed for 23 hours. After completion of the reaction, the reaction mixture was poured into a saturated sodium chloride solution (5 ml) and ethyl acetate was used for extraction. The extracted solution was dried using anhydrous sodium sulfate and the solvent was removed by evaporation. The residue was subjected to silica gel thin layer chromatography effected by using a solvent system of chloroform and methanol (9:1 v/v). The development was effected twice. The band around Rf=0.49 was collected and eluted by using a mixture of chloroform and methanol (9:1 v/v). The solvent was removed from the reaction product by evaporation in vacuo to results in the desired product in the form of pale brown solids (2.6 mg; yield 32.5%). The Rf value of the starting 10-decarbamoylmitomycin D on TLC was 0.52. The physical properties of the final product are as follows.

Mass spectrum: Molecular ion peak at m/e 291.

PMR spectrum (in Py.-$d_5$, δppm):

1.96 (s, 3H), 2.16 (dd, 1H), 2.24 (s, 3H), 2.74 (d, 1H), 3.67 (dd, 1H), 3.91 (dd, 1H), 4.39 (dd, 1H), 4.56 (d, 1H), 4.66 (dd, 1H).

IR spectrum (KBr tablet method, $cm^{-1}$):

3320 (m), 1595 (s), 1541 (vs), 1444 (s), 1347 (m).

From these characteristics, this substance was identified as 9-epi-10-decarbamoylmitomycin D.

9-epi-10-decarbamoyl-10-phenoxycarbonylmitomycin D [Step 3]:

A mixture of 9-epi-10-decarbamoylmitomycin D and 10-decarbamoylmitomyicin D (1:1, 14.6 mg) was dissolved in anydrous pyridine (0.5 ml) which was then added with phenyl chloroformate (9.5 μl). The mixture was stirred for 4 hours and poured into a cold aqueous saturated solution of sodium hydrogen carbonate (10 ml). The mixture was extracted with ethyl acetate and the extracted solution was dried over anhydrous sodium sulfate, followed by removal of the solvent by evaporation in vacuo. The residue was subjected to silica gel chromatography using a solvent system of chloroform and acetone (7:3 v/v) to obtain a pale brown solid (6.0 mg; yield 58.2%). When developed by silica gel thin layer chromatography using a solvent system of chloroform and acetone (3:2 v/v), this substance showed a Rf value of 0.45, while the corresponding Rf value of 10-decarbamoyl-10-phenoxycarbonylmitomycin D determined under the same conditions was 0.34.

The physical characteristics of the final product were as follows.

Mass spectrum: Molecular ion peak at m/e 411.
PMR spectrum (in Py.-$d_5$; $\delta$ppm):
2.02 (s, 3H), 2.29 (s, 3H), 2.29 (dd, 1H), 2.73 (d, 1H), 3.71 (dd, 1H), 4.20 (dd, 1H), 4.57 (d, 1H), 4.93 (dd, 1H), 5.46 (dd, 1H), 7.37–7.42 (5H).

From these characteristics, this substance was identified as 9-epi-10-decarbamoyl-10-phenoxycarbonylmitomycin D.

9-epi-mitomycin D [Step 4]:
9-epi-10-decarbamoyl-10-phenoxycarbonylmitomycin D (6.0 mg) was dissolved in chloroform (1.5 ml). When ammonia was blown into the solution for 30 minutes, the solution was cooled in a dry ice-methanol bath. Then the reaction was effected for 1.5 hours under cooling conditions. After completion of the reaction, nitrogen gas was blown into the reaction mixture to remove ammonia and the solvent was also remove by evaporation in vacuo. The residue was purified by silica gel chromatography using a solvent system of chloroform and methanol (85:15 v/v) to obtain a pale brown solid (4.5 mg; yield 92.5%) having the following physical characteristics.

Mass spectrum: Molecular ion peak at m/e 334.
PMR spectrum (in Py.-$d_5$; $\delta$ppm):
2.00 (s, 3H), 2.20 (dd, 1H), 2.30 (s, 3H), 2.72 (d, 1H), 3.69 (dd, 1H), 4.18 (dd, 1H), 4.58 (d, 1H), 4.92 (dd, 1H), 5.46 (dd, 1H).

IR spectrum (KBr tablet method): As shown in FIG. 1. From these characteristics, this substance was identified as 9-epi-mitomycin D.

EXAMPLE 2

9-epi-mitomycin B [Step 7]: 9-epi-mitomycin D (17.5 mg) was dissolved in 0.1 N caustic soda solution (10 ml) which was then stirred for 6 hours at room temperature. The reaction solution was adjusted to a pH of 4 with a diluted hydrochloric acid solution and extracted with ethyl acetate. The extracted solution was washed with water and dried over anhydrous sodium sulfate. The solvent was removed by evaporation under reduced pressure and the residue was dissolved in methanol (5 ml). When an excessive amount of diazomethane-ethanol solution was dropwise added to the solution and the reaction was effected for 10 minutes, the reaction mixture was cooled with ice and stirred. The solvent was removed from the reaction mixture by evaporation under reduced pressure and the solution was treated by silica gel column chromatography using a solvent system of chloroform and methanol (95:5 v/v) to result in the crystals coloured in dark purple (4.8 mg; yield 26.3%) having the following physical characteristics:

Mass spectrum: Molecular ion peak at m/e 349.
PMR spectrum (in Py.-$d_5$; $\delta$ppm):
1.80 (s, 3H), 2.20 (dd, 1H), 2.28 (s, 3H); 2.70 (d, 1H), 3.58 (dd, 1H), 3.98 (s, 3H), 4.07 (dd, 1H), 4.22 (d, 1H), 4.85 (dd, 1H), 5.38 (dd, 1H).

IR spectrum (KBr tablet method):
As shown in FIG. 2.

From these characteristics, the final product was identified as 9-epi-mitomycin B.

EXAMPLE 3

9-epi-mitomycin D [Step 8]:
9-epi-mitomycin B (8.5 mg) was dissolved in methanol (2 ml) containing ammonia (6% by weight) and stirred for 6 hours at room temperature. After completion of the reaction, the solvent was removed by evaporation in vacuo. When the residue was purified by silica gel column chromatography using a solvent system of chloroform and methanol (85:15 v/v), a pale brown solid (7.1 mg; yield 87.3%) was obtained. This substance was identified as 9-epi-mitomycin D because the mass spectrum, PMR spectrum and IR spectrum of this substance were the same as those of the product of Example 1.

Reference 1

9a-O-demethyl-mitomycin G [step 6]:
9-epi-mitomycin D (10 mg) was dissolved in tetrahydrofuran (0.5 ml). To the solution was added 1,5-diazabicyclo[5,4,0]undec-5-ene (20 mg) and the solution was refluxed for 18 hours. After completion of the reaction, the solvent was removed by evaporation in vacuo, and the residue was purified by silica gel column chromatography using a solvent system of chloroform and acetone (3:2 v/v) to give the desired dark green needle crystals (4.4 mg; yield 53.8%) having the following physical characteristics.

Mass spectrum: Molecular ion peak at m/e 273.
PMR spectrum (in Py.-$d_5$; $\delta$ppm):
1.92 (s, 3H), 2.15 (s, 3H), 2.25 (dd, 1H), 2.57 (d, 1H), 3.70 (dd, 1H), 4.69 (d, 1H), 5.75 (d, 1H), 6.45 (d, 1H).

From these characteristics, this substance was identified as 9a-O-demethylmitomycin G.

Reference 2

1a-N-methylmitomycin A (mitomycin F) [Step 5]:
9-epi-mitomycin B (20 mg) was dissolved in a mixture of dimethylformamide and benzene (1:3 v/v) (1.6 ml) which was cooled in a salt-ice bath with stirring under nitrogen stream. Sodium hydride (50%; 10 mg) and dimethyl sulfate (14 $\mu$l) were simultaneously added to the solution which was then stirred for 40 minutes. After completion of the reaction, the excessive amount of sodium hydride was decomposed using ethyl acetate saturated with water. After extraction using ethyl acetate, the extracted solution was washed with water and dried over anhydrous sodium sulfate. The solvent was removed from the reaction mixture by evaporation in vacuo and the residue was purified by using silica gel column chromatography using a solvent system of chloroform and acetone (3:2 v/v) to give reddish purple crystals (10.6 mg; yield 51.0%) having the following characteristics, from which the final product was identified as 1a-N-methylmitomycin A (mitomycin F).

Mass spectrum: Molecular ion peak at m/e 363.
PMR spectrum (in $CD_3OD$; $\delta$ppm):
1.83 (s, 3H), 2.27 (s, 3H), 2.43 (dd, 1H), 2.52 (d, 1H), 3.21 (s, 3H), 3.42 (dd, 1H), 3.57 (dd, 1H), 4.00 (s, 3H), 4.00 (d, 1H), 4.18 (dd, 1H), 4.70 (dd, 1H).

We claim:
1. 9-epi mitomycin B.
2. The compound of claim 1 in substantially pure form.
3. 9-epi mitomycin D.
4. The compound of claim 3 in substantially pure form.

* * * * *